US00PP23704P2

(12) United States Plant Patent
Sakazaki

(10) Patent No.: US PP23,704 P2
(45) Date of Patent: Jul. 2, 2013

(54) ***PHLOX* PLANT NAMED 'PPPHL0623'**

(50) Latin Name: ***Phlox subulata*×*stolonifera***
Varietal Denomination: PPPHL0623

(75) Inventor: Ushio Sakazaki, Hikone (JP)

(73) Assignee: Amerinova Properties, Bonsall, CA (US)

( * ) Notice: Subject to any disclaimer, the term of this patent is extended or adjusted under 35 U.S.C. 154(b) by 86 days.

(21) Appl. No.: 13/317,218

(22) Filed: Oct. 12, 2011

(51) Int. Cl.
*A01H 5/00* (2006.01)

(52) U.S. Cl.
USPC ..... Plt./320

(58) Field of Classification Search
USPC ..... Plt./320
See application file for complete search history.

*Primary Examiner* — Susan McCormick Ewoldt
(74) *Attorney, Agent, or Firm* — Cassandra Bright

(57) ABSTRACT

A new and distinct *Phlox* cultivar named 'PPPHL0623' is disclosed, characterized by light lavender flowers, vigorous plant growth and early flowering, with blooms produced over a long period of time. Plants have a good resistance to powdery mildew. The new variety is a *Phlox*, normally produced as an outdoor ornamental plant for containers or gardens.

2 Drawing Sheets

Figure 1:
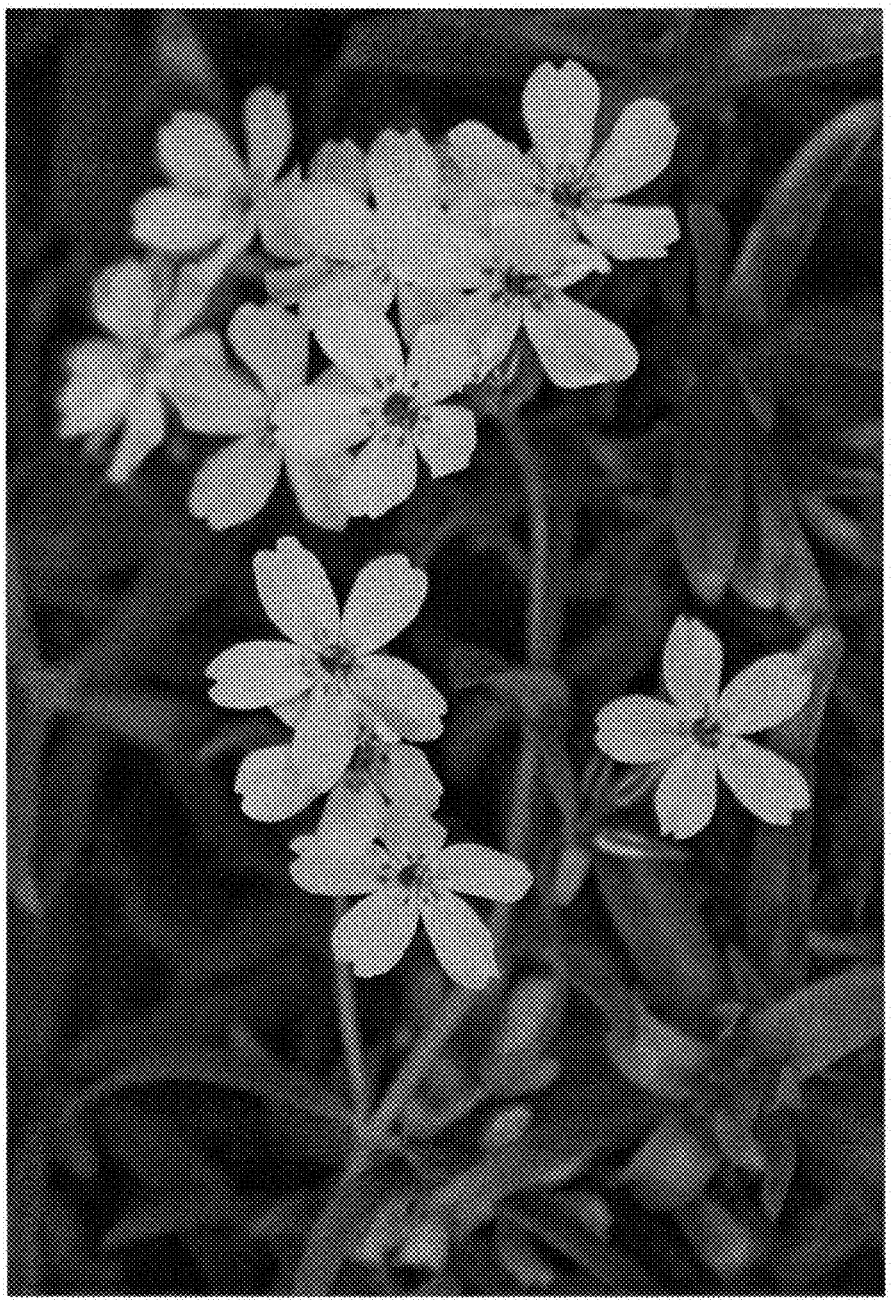

Latin name of the genus and species: *Phlox subulata*× *stolonifera*.
Variety denomination: 'PPPHL0623'.

BACKGROUND OF THE INVENTION

The new cultivar was discovered as a result of a planned breeding program directed by the inventor, Ushio Sakazaki, a citizen of Japan. The seed parent is an unnamed, unpatented variety of *Phlox subulata* and the pollen parent is an unnamed, unpatented variety of *Phlox stolonifera*. The cross resulting in 'PPPHL0623' was made Apr. 11, 2005. The new variety was discovered Sep. 15, 2006, by the inventor in a non-commercial nursery in Higashiomi Shiga, Japan.

Asexual reproduction of the new cultivar 'PPPHL0623' by vegetative cuttings was first performed Sep. 20, 2006 at a non-commercial nursery in Higashiomi Shiga, Japan. Multiple generations have since been produced and have shown that the unique features of this cultivar are stable and reproduced true to type in successive generations.

SUMMARY OF THE INVENTION

The cultivar 'PPPHL0623' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PPPHL0623' These characteristics in combination distinguish 'PPPHL0623' as a new and distinct *Phlox* cultivar:

1. Vigorous growth habit, compared to existing *Phlox subulata* varieties.
2. Early flowering.
3. Long flowering period.
4. Good resistance to powdery mildew.
5. Flowers of a light lavender color.

PARENT COMPARISON

Plants of the new cultivar 'PPPHL0623' are similar to plants of the seed parent, *Phlox subulata*, unnamed, in most horticultural characteristics, however, plants of the new cultivar 'PPPHL0623' produce flowers over a significantly longer period than the seed parent. 'PPPHL0623' has lavender colored flowers, whereas the seed parent produces flowers that are white. Additionally, plants of the new variety are much more vigorous, and produce larger flowers than the seed parent.

Plants of the new cultivar 'PPPHL0623' are similar to plants of the pollen parent *Phlox stolonifera*, unnamed, in most horticultural characteristics, however, plants of the new cultivar 'PPPHL0623' produce flowers over a significantly longer period than the pollen parent. 'PPPHL0623' has a lavender colored flower, whereas the pollen parent produces flowers that are white. Additionally, the new variety has smaller foliage than the pollen parent.

COMMERCIAL COMPARISON

'PPPHL0623' can be compared to the commercial variety *Phlox subulata* 'Emerald Blue', unpatented. The two varieties are very similar in most horticultural characteristics, however, plants of 'PPPHL0623' produce larger flowers, and flowers throughout Spring and Summer, whereas 'Emerald Blue' flowers only during the Spring. Additionally, plants of 'PPPHL0623' are more mounding growth habit compared to the flat, mat forming habit of 'Emerald Blue'. Flower color also differs, as the new variety produces flowers that are more lavender and less blue in shade than 'Emerald Blue'.

'PPPHL0623' can be compared to the commercial variety *Phlox subulata* 'Emerald Cushion Blue', unpatented. The two varieties are very similar in most horticultural characteristics, however, plants of 'PPPHL0623' produce larger flowers, and flowers throughout Spring and Summer, whereas 'Emerald Cushion Blue' flowers only during the Spring. Additionally, plants of 'PPPHL0623' are more mounding growth habit compared to the flat, mat forming habit of 'Emerald Cushion Blue'. Flower color also differs, as the new variety produces flowers that are more lavender and less blue in shade than 'Emerald Cushion Blue'.

BRIEF DESCRIPTION OF THE PHOTOGRAPHS

The accompanying photograph in FIG. 1 illustrates in full color a close up view of flowers of 'PPPHL0623'.

Figure 2:
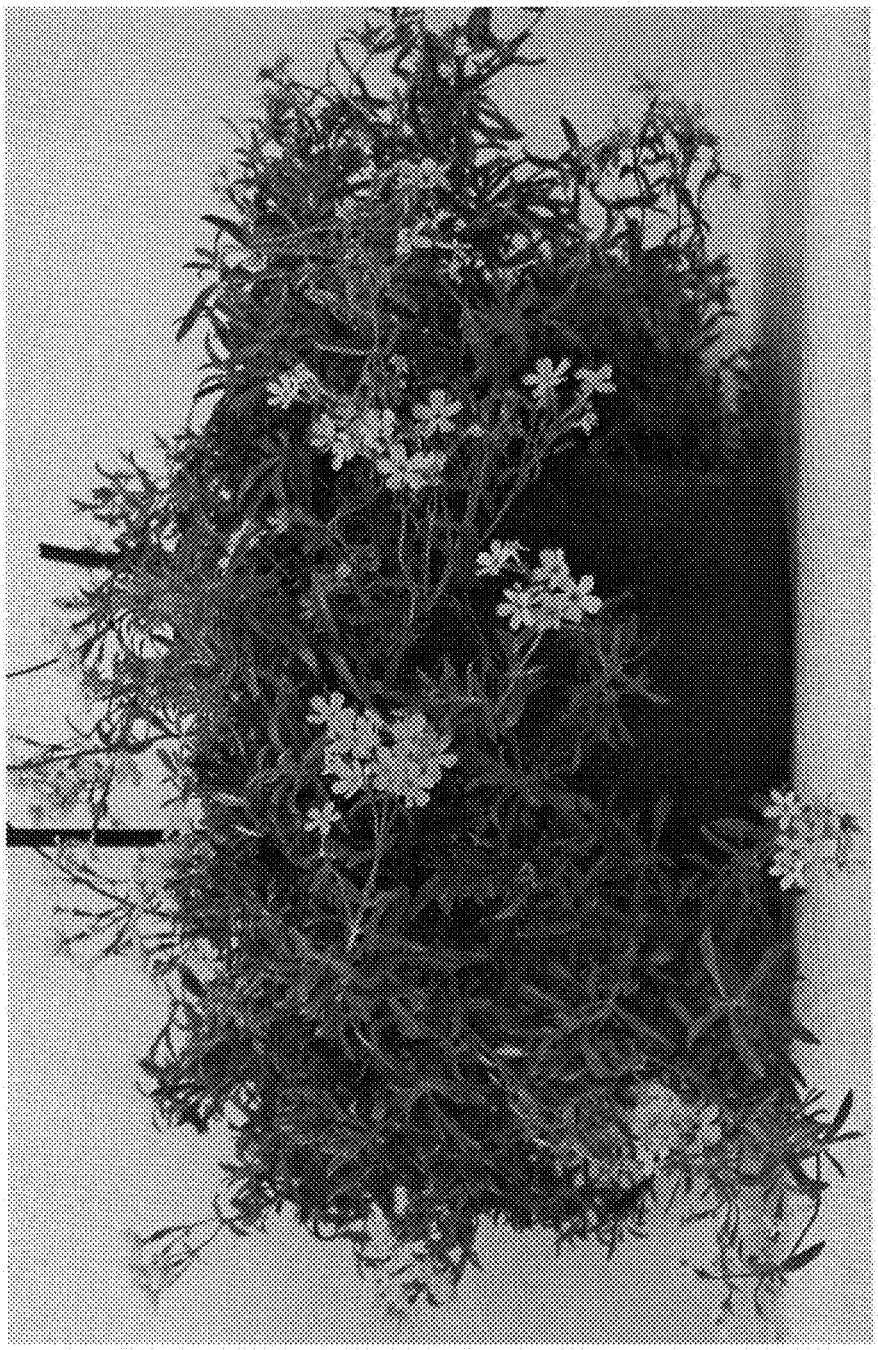

FIG. 2 illustrates in full color a typical plant of 'PPPHL0623' grown in a poly house, in Bonsall, Calif., in a commercial 10 inch container. Age of the plant photographed is approximately 28 weeks from a rooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001 except where general terms of ordinary dictionary significance are used. The following observations and measurements describe 'PPPHL0623' plants grown in a poly house, in Bonsall, Calif., in a commercial 10 inch container. The growing temperature ranged from 60° F. to 75° F. daytime and 50° F. to 60° F. at night. No chemical treatments were given. Measurements and numerical values represent averages of typical plant types.

Botanical classification: *Phlox subulata×stolonifera* 'PPPHL0623'.

PROPAGATION

Time to initiate roots during summer: Approximately 5 days at temperatures between 17° C. and 29° C.
Time to initiate roots during winter: Approximately 6 days at temperatures between 17° C. and 21° C.
Time to produce a rooted cutting: 33 days.
Root description: Fine, fibrous, moderately dense rooting habit.

PLANT

Growth habit: Mounding, spreading.
Pot size of plant described: 25 cm diameter basket.
Age of plant described: Approximately 25 Weeks.
Height:
- *To top of flowers*.—Approximately 14 cm.
- *To top of foliage plane*.—Approximately 11 cm.

Plant spread: Approximately 50 cm.
Growth rate: Rapid.
Branching characteristics: Very well branched.
Length of primary lateral branches: Approximately 15 cm.
Quantity of primary lateral branches: More than 50 per plant.
Characteristics of primary lateral branches:
- *Form*.—Round.
- *Diameter*.—Approximately 0.2 cm.
- *Color*.—Near RHS Yellow-Green 144C.
- *Texture*.—Densely pubescent. Hairs minute, less than 0.1 cm.
- *Strength*.—Flexible, moderately strong.

Internode length: Average between 1 to 2.5 cm.

FOLIAGE

Leaf:
- *Arrangement*.—Opposite.
- *Quantity*.—Approximately 18 per branch.
- *Average length*.—Approximately 3.0 cm.
- *Average width*.—Approximately 0.6 cm.
- *Shape of blade*.—Narrowly oblanceolate.
- *Apex*.—Acute.
- *Base*.—Blunt.
- *Margin*.—Entire.
- *Texture of top surface*.—Very minutely pubescent.
- *Texture of bottom surface*.—Very minutely pubescent.
- *Aspect*.—Somewhat recurved.
- *Color*.—Young foliage upper side: Near RHS Green 143B. Young foliage under side: Near RHS Green 143C. Mature foliage upper side: Near RHS Green 137A. Mature foliage under side: Near RHS Green 137C.
- *Venation*.—Type: Pinnate. Venation color upper side: Indistinguishable from foliage coloration. Venation color under side: Indistinguishable from foliage coloration.
- *Petiole*.—Sessile, petiole not present.

FLOWER

Natural flowering season: Spring through Summer.
Inflorescence and flower type and habit: Clustered cymes of salverform flowers. 2 to 3 cymes, of 3 to 5 flowers.
Rate of flower opening: 3 to 5 days from bud to fully opened flower.
Flower longevity on plant: Approximately 1 week.
Approximate quantity of flowers per plant: Approximately 80 to 100.
Persistent or self-cleaning: Persistent.
Inflorescence:
- *Depth*.—Approximately 9 cm.
- *Width*.—Approximately 7 cm.

Individual cyme:
- *Depth*.—Approximately 4 cm.
- *Width*.—Approximately 3 cm.

Bud:
- *Shape*.—Cylindric.
- *Length*.—Approximately 1.2 cm.
- *Diameter*.—Approximately 0.3 cm.
- *Color*.—Near RHS Purple 76D.

Flower size:
- *Length*.—Approximately 1.5 cm.
- *Flower tube length*.—Approximately 1.0 cm.
- *Flower tube diameter at basal end*.—Approximately 0.3 cm.
- *Flower tube diameter at distal end*.—Approximately 1.5 cm.

Petals:
- *Length from throat*.—Approximately 0.5 cm.
- *Width*.—Approximately 0.5 cm.
- *Quantity*.—5.
- *Texture*.—Glabrous.
- *Apex*.—Bi-lobed, blunt lobes.
- *Margin*.—Entire.

Color:
- *When opening*.—Upper surface: Near RHS Purple 76B. Lower surface: Near RHS Purple 76BC.
- *Fully opened*.—Upper surface: Near RHS Violet 85B, dots at throat attachment near Violet 86B. Lower surface: Near RHS Purple 76A. Flower throat (inside): Near RHS Purple 76C. Flower throat, visible rim: RHS Violet 86B. Flower tube (outside): Near RHS Purple 76C.
- *Fading*.—Petals fading to: Near RHS Purple 76B, all surfaces.

Calyx/sepals:
- *Quantity per flower*.—5.
- *Shape*.—50% fused together, linear shape.

*Length*.—Approximately 0.7 cm.
*Width*.—Approximately 0.2 cm.
*Apex*.—Acute.
*Base*.—Fused.
*Margin*.—Entire.
*Texture*.—Glabrous.
*Color*.—Upper Surface: Near RHS Green 137A. Lower Surface: Near RHS Green 137A.

Peduncle:
*Length*.—Average 4 cm.
*Diameter*.—Average 0.15 cm.
*Color*.—Near RHS Green 143C.
*Texture*.—Lightly pubescent.
*Orientation*.—Approximately 75° to 90° angle from stem, undulating.

Pedicel:
*Length*.—Approximately 1.1 cm.
*Diameter*.—Approximately 0.1 cm.
*Color*.—Near RHS Green 143C.
*Texture*.—Very minutely pubescent.
*Orientation*.—Approximately 30° to 45° angle from peduncle, undulating.

Fragrance: Musty.

REPRODUCTIVE ORGANS

Stamens:
*Number*.—5.
*Filament length*.—Fused to petals, unfused portion 0.1 cm.

Anthers:
*Length*.—0.1 cm.
*Shape*.—Linear.
*Color*.—Near RHS White N155A.
*Pollen*.—Color: Near Yellow 13A. Quantity: Moderate.

Pistil:
*Number*.—1.
*Length*.—0.7 cm.
*Style*.—Length: 0.6 cm.
*Color*.—Near RHS White N155A.
*Stigma*.—Shape: forked. Color: Near RHS Yellow 4B. Ovary Color: Near RHS Yellow-Green 145B.

OTHER CHARACTERISTICS

Seeds and fruits: Not observed to date.

Disease/pest resistance: Resistance to Powdery Mildew has been observed.

Temperature tolerance: Tolerant to least −1° C. without damage. Upper temperature tolerance to at least 30° C.

What is claimed is:

1. A new and distinct cultivar of *Phlox* plant named 'PPPHL0623' as herein illustrated and described.

* * * * *